United States Patent [19]

Boggs et al.

[11] 4,391,516

[45] Jul. 5, 1983

[54] METHOD OF DETERMINING AN INDEX OF REFRACTION PROFILE OF AN OPTICAL FIBER

[75] Inventors: Luther M. Boggs, Dunwoody; William B. Gardner, Chamblee, both of Ga.

[73] Assignees: Western Electric Co., Inc., New York, N.Y.; Bell Telephone Laboratories, Incorporated, Murray Hill, N.J.

[21] Appl. No.: 941,824

[22] Filed: Sep. 11, 1978

[51] Int. Cl.³ .......................................... G01N 21/45
[52] U.S. Cl. .................................. 356/73.1; 356/361
[58] Field of Search ............................... 356/73.1, 361

[56] References Cited

U.S. PATENT DOCUMENTS 3,879,128  4/1975  Presby ........................... 356/361 X

OTHER PUBLICATIONS

Marhic et al., "Nondestructive Refractive-Index Profile Measurements of Clad Optical Fibers", *Applied Physics Letters*, vol. 26.

Saunders et al., "Nondestructive Interterometric Measurements of the Delta and Alpha of Clad Optical Fibers", *Applied Optics*, vol. 16, No. 9, pp. 2368–2371, 9/77.

Kokubun et al., "Precise Measurement of the Refractive Index Profile of Optical Fibers by a Nondestructive Interference Method", *The Transactions of the IECE of Japan*, vol. E60, No. 12, pp. 702–707, 12/77.

Hunter et al., "Mach-Zehnder Interferometer Data Relation Method for Retractively Inhomogeneous Test Objects", *Applied Optics*, vol. 14, No. 3, pp. 634–639, 3/75.

*Primary Examiner*—John K. Corbin
*Assistant Examiner*—Matthew W. Koren
*Attorney, Agent, or Firm*—David P. Kelley

[57] ABSTRACT

A method is disclosed for determining the index of refraction profile of a stepped or graded index type optical fiber having a core encased within a surrounding cladding. An interferogram is formed with a beam of radiant energy passed transversely through the optical fiber. Fringe line shift is measured at a series of points corresponding to a series of mutually parallel ray chord paths extending through the core at mutually diverse minimum radial distances from the core axis. That portion of the measured fringe line shift attributable to discrete differences in indices of refraction of cylindrical core ring portions of thicknesses defined by successive minimum radial distances in the series of ray paths and that of the cladding is sequentially calculated from the outermost core ring portion inwardly towards the core center.

7 Claims, 8 Drawing Figures

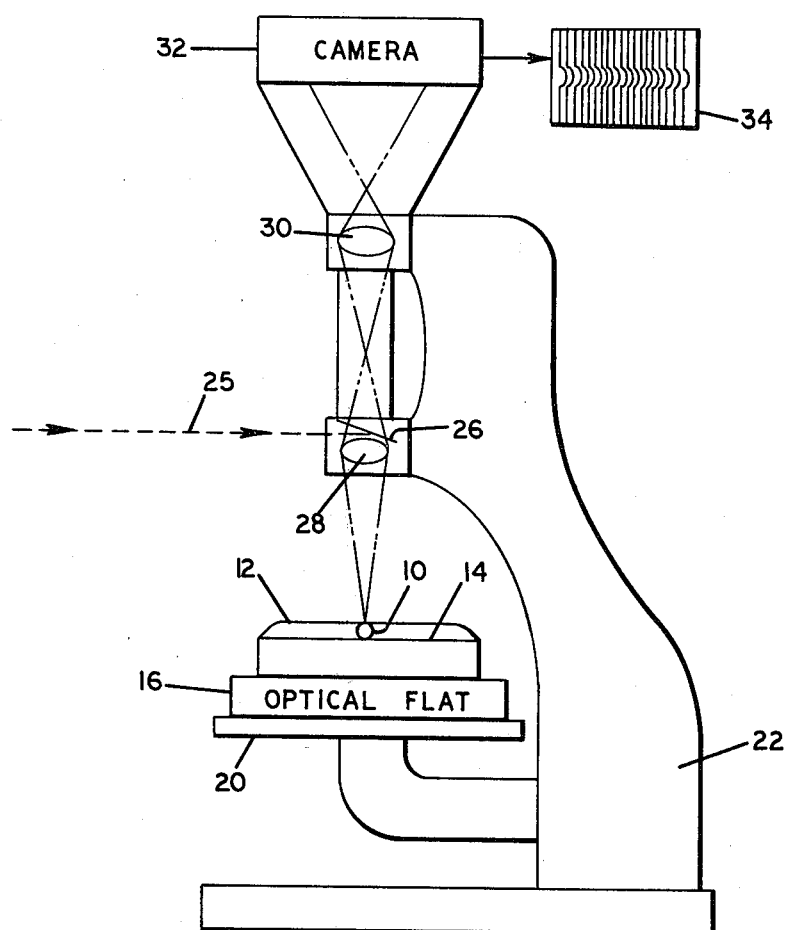
Fig_1
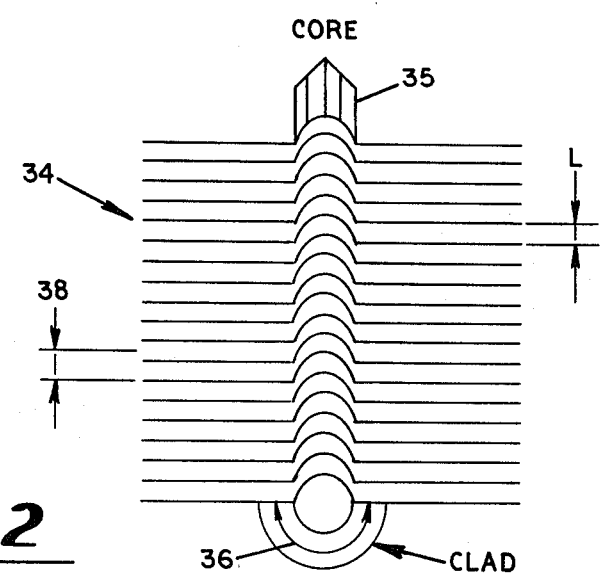
Fig_2

METHOD OF DETERMINING AN INDEX OF REFRACTION PROFILE OF AN OPTICAL FIBER

TECHNICAL FIELD

This invention relates to optical fibers of the type having graded index of refraction cores, and particularly to methods of determining the index of refraction profiles of such fibers.

BACKGROUND OF THE INVENTION

Optical fibers are being developed today for usage in the communications industry. One type of such optical fiber is that termed stepped index which comprises an elongated, transparent core of uniform index of refraction which is encased within a surrounding transparent cladding of a lower refractive index. For communication purposes a series of light pulses are transmitted through the core; however the various light rays of a pulse follow different paths within the core as they reflect back and forth along the boundary of core and cladding. As a consequence the pulse length elongates during core travel which in turn restricts fiber bandwidth.

In order to increase bandwidth and thereby provide a multimode, high-capacity optical fiber communications system another type of optical fiber has been developed which is termed graded index. With this type of optical fiber the fiber core has an index of refraction that varies radially from the core axis to the core periphery. Ideally, the distribution of refractive indices within the core should be such as to cause all light rays of a pulse to travel along the fiber at the same axial velocity regardless of traversed path length variations. In actuality, of course, there will be some deviation from optimum refractive index distribution of the core made during fiber manufacture. The manufacturer must therefore monitor this distribution to insure that various variations remain within specified tolerances.

Heretofore, the most accurate method of monitoring such index of refraction distribution profiles has been that of the slab method. This involves a rather elaborate, tedious and time consuming preparation of a fiber sample whereby a thin slide is cut out from the fiber and polished to a high degree of flatness and parallelism of opposed surfaces. The samples, which are then examined with an interference microscope, act as phase objects that displace in the core region the normally straight parallel fringe lines of the microscope output field. The fringe displacements or shifts are proportional to differences in the indices of refraction within the various radial regions of the core and that of the cladding.

Recently, non-destructive approaches have been taken in determining index distribution profiles. These are disclosed in the article by Hunter and Schreiber titled "Mach-Zehnder Interferometer Data Reduction Method for Refractively Inhomogeneous Test Objects", Applied Optics, Vol. 14, No. 3, (March, 1975), in the article by Marhic, Ho and Epstein titled "Nondestructive Refractive-Index Profile Measurement of Clad Optical Fibers", Applied Physics Letters 26 (1975), and also in the article by Kokubun and Iga titled "Precise Measurement of the Refractive Index Profile of Optical Fibers by a Nondestructive Interference Method", Transactions of the IECE of Japan, Vol. E60, No. 12 (December, 1977). A common aspect of these methods is that a beam of light is passed transversely through the optical fiber and into a Mach-Zehnder interferometer. Hunter and Schreiber originally concluded that fringe shift contributions due to the refractive medium could not be reduced with an inverted Abel integral equation to determine accurately the internal index of refraction distribution that was thought to be possible since the refraction angles of probing rays would be known. Kokubun and Iga however found a mathematical error in the integral equation used by Hunter and Schreiber and in turn concluded that a correct algorithm had indeed been found for non-destructive index determination with transverse illumination.

Notwithstanding the clarification provided by Kokubun and Iga, the solution of the integral equation remains accomplishable only by an extremely complex method of successive approximation involving a Taylor series expansion. The change in index of refraction of the core is thus considered as being in a series of discrete steps as a function of core radius. The index of refraction at any one ring, $N_r$, may be stated as $N_r = N_o - \Delta N(r/a)^\alpha$ where r designates radial position, as is the outside radius of the outermost ring, $N_o$ is the refractive index at core center where r=o, $\Delta N$ is the difference in refractive index between core center and cladding where r=o and $\alpha$ is a dimensionless number that characterizes the shape of the core index profile.

In addition to the just described complexity of the prior art approaches for determining index profile, they also have been based on the assumption that the core is circular and, in general, that $\alpha$ remains uniform throughout the core, which it often does not. For example, some optical fibers have a barrier layer at the interface of core and cladding which causes the index at this position actually to be less than that of the cladding. In such a situation the above equation becomes completely invalid as a model. Furthermore, results of the successive approximation method have not been shown in actual comparisons with slab measurements on the same fibers.

Recently, in a 1977 article by Saunders and Gardner which appeared in Vol. 16 of Applied Optics titled "Nondestructive Interferometric Measurement of the Delta and Alpha of Clad Optical Fibers" another, similar method is discussed. The analysis here however is restricted to power law profiles characterized by two constants, namely the refractive index difference between the maximum value at core center and the cladding value, and the power law coefficient which is the same profile shape characterization $\alpha$. Therefore this analysis also assumes a circular core and a uniform $\alpha$ throughout the core fiber.

Accordingly, it is a general object of the present invention to provide an improved method of determining an index of refraction profile of an optical fiber.

More specifically, it is an object of the invention to provide an improved, non-destructive type method of determining an optical fiber index of refraction profile of the type wherein an interferogram is formed with light passed transversely through the fiber.

Another object of the invention is to provide a method of determining an index of refraction profile of the type described which does not require assumption of any particular functional shape of index distribution.

SUMMARY OF THE INVENTION

In one preferred form of the invention a method is provided for determining an index of refraction profile of an optical fiber having a core encased within a layer of cladding. The method comprises the step of forming an interferogram with a beam of radiant energy passed transversely through the optical fiber whereby the interferogram displays a pattern of mutually spaced interference fringe line shifted from a reference line by distances determined by differences between the indices of refraction radially through the fiber core and that of the fiber cladding. The interferogram fringe line shifts are measured at points along a fringe line corresponding to a series of mutually parallel ray chord paths extending through the core at mutually diverse minimum radial distances from the core axis. That portion of the measured fringe line shift attributable to discrete differences in the indices of refraction of cylindrical core ring portions of thicknesses defined by successive minimum radial distances in the series of ray paths and that of the cladding is sequentially calculated from the outermost core ring portion inwardly towards the core center.

BRIEF DESCRIPTION OF THE DRAWINGS

FIG. 1 is a schematic diagram of a system of the double pass type for forming an interferogram which may be used in practicing the present invention.

FIG. 2 is a illustration of an interferogram made with the system of FIG. 1 or FIG. 3 in practicing the method of this invention.

DETAILED DESCRIPTION

Figure 3:
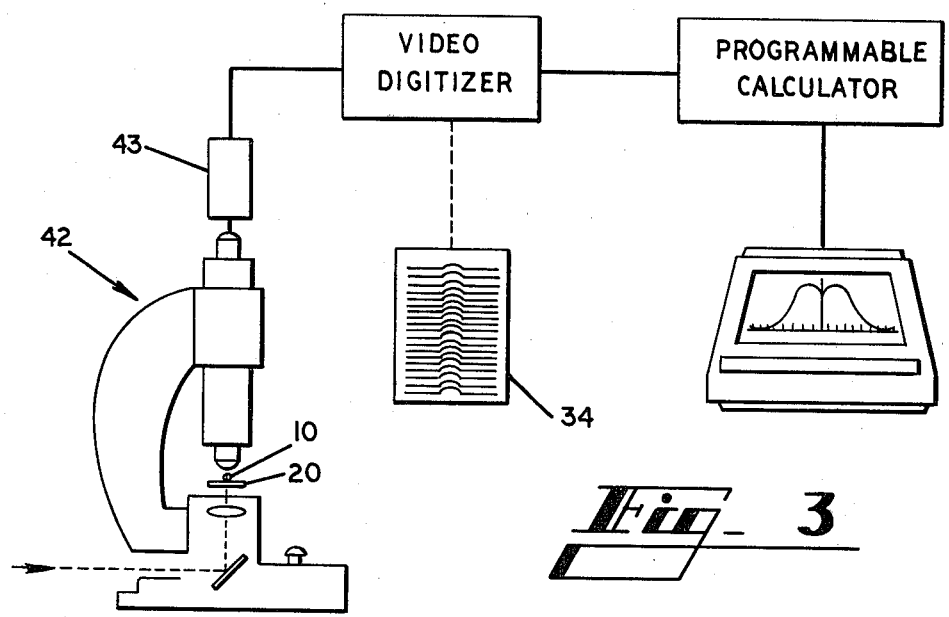
FIG. 3 is a schematic diagram of a system of the single pass type for forming and automatically analyzing an interferogram in practicing the present invention.

Referring now in more detail to the drawing, there is schematically shown in FIG. 1 a system for forming an interferogram with light of narrow optical frequency bandwidth, such as that which may be provided by a laser, passed transversely twice through an optical fiber under test. A graded index type optical fiber 10 is seen to be submerged in an oil bath 12 having an index of refraction matching test of the fiber cladding atop an optical flat 16 providing a mirror surface 14. The bath and mirror are located atop an adjustable stage 20 projecting from a microscope base 22. A beam of light 25 emitted from a He-Ne laser is directed through an unshown moving diffuser onto a beam splitter 26 component of an Michelson interferometer objective 28 and then transversely through the optical fiber 10. Alternatively, non-coherent, filtered light may be used. The beam is then reflected off of the mirror 14 back through the fiber, the objective end beam splitter, and through the microscope eyepiece 30 onto a camera 32. In this manner an interferogram 34 is conventionally formed.

With reference next to FIG. 2 the interferogram 34 is seen to be formed of a number of interference fringe lines spaced apart a distance L. A center portion 35 of each line is seen to be curved while adjacent, straddling side portions 36 are straight and mutually parallel. The side portions thus correspond to the cylindrical layer of fiber cladding and index matching oil while the center portion corresponds to the fiber core which again is of a non-uniform, graded refractive index. Representative maximum fringe shift due to the core is shown at 38.

As will hereinafter be described in greater detail, the present method ignores bending of the sensing light rays as they pass twice through the core, both towards and away from the mirror. In actuality ray bending does, of course, occur in an amount computable by successive applications of Snell's law. However, this error can be reduced by a factor of about six where a single pass approach is utilized. In addition, the change in the exit angle caused by the core is only about half that of the double pass case.

FIG. 3 schematically illustrates just such a single pass system for forming an interferogram with a beam of light which passes only once through the optical fiber core under index profile examination. This system is seen to include a Leitz dual-beam single-pass transmission interference microscope 42 commonly used in examining polished slab samples. This microscope is essentially a combination of two microscopes and an interferometer whereby the magnified image of the object and the interference pattern are superimposed. Here again the optical fiber is submerged in a bath of oil having an index of refraction matching that of the fiber cladding in the sample arm of the interference microscope. A similar thickness of matching oil is placed in the reference arm. The output field of the microscope is detected with a vidicon camera 43. The camera video signal is transmitted to a video digitizer having the capability of addressing x, y coordinates and encoding picture elements in the picture frame. A video output display monitor is also connected to the digitizer ouptut for continuous observation of the interferogram 34. The video digitizer also provides intensity information to a calculator programmed for calculations as hereinafter described at the coordinates addressed by the calculator. At each radial position through the fiber core a set of intensity data is obtained corresponding to the amount of light present at each point across the fringe. The darkest point locates a fringe center. The calculated index profile is finally displayed on a plotter.

Figure 4:
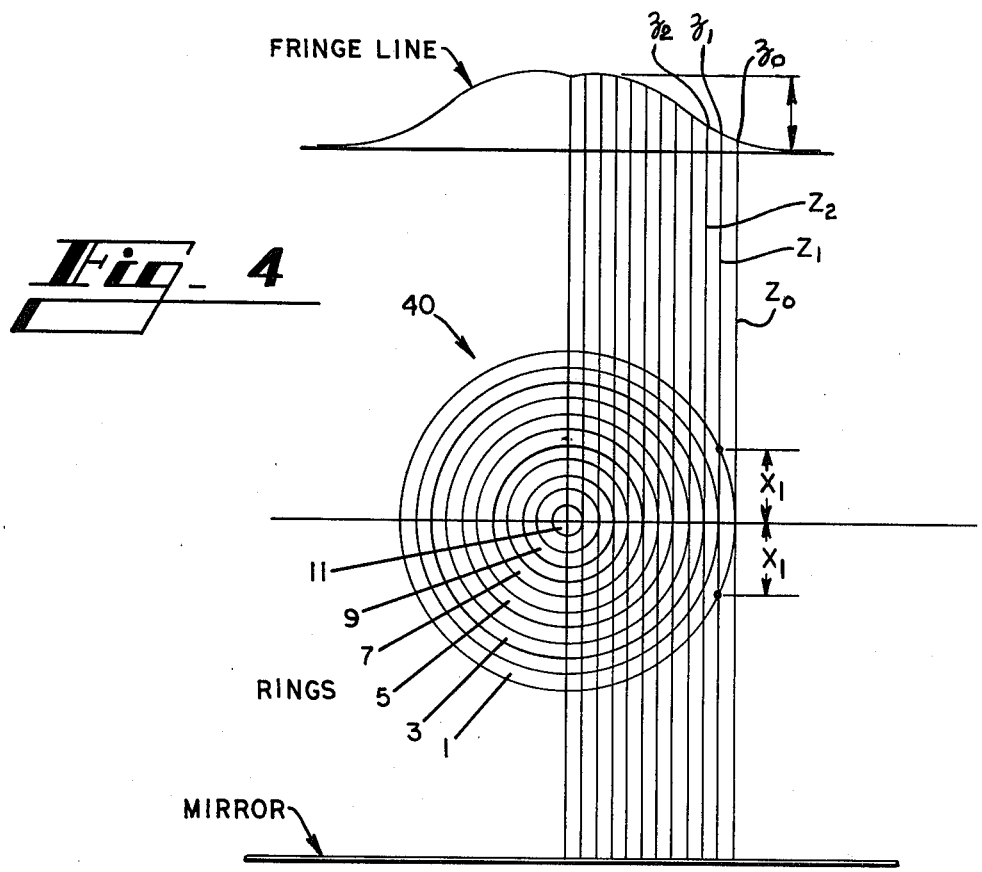
FIG. 4 is a schematic diagram of an optical fiber transverse section and projected interferogram fringe line using the system shown in FIG. 1.
Figure 5:
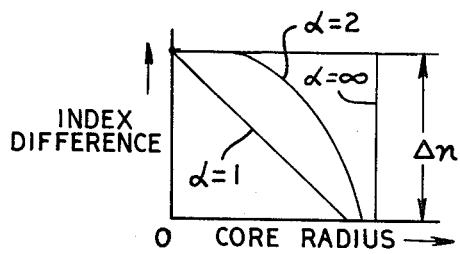
FIG. 5 is a graphic illustration of characterizations of graded core index of refraction profiles in general.

With reference next to FIG. 4 the manner in which information is extracted from the interferogram, here made with the double pass system, is graphically illustrated. It should be understood however that this same general procedure is applicable to the single pass method. First, it is assumed that all light rays do pass through the fiber core without deflection, using only the fact that their phases are retarded according to the lengths of their optical paths. A further assumption made is that fiber core consists of a number of concentric rings, of either equal or unequal thicknesses, but with each ring having a constant index of refraction. Ray bending between the mirror and core is also neglected. The profile is derived by evaluating the refractive indices, step by step, beginning at the outermost ring and proceeding towards the core center. In other words, the index of refraction of any inner ring is determined only after the index values of all other, surrounding rings at greater radial position from core center have first been determined.

Figure 6:
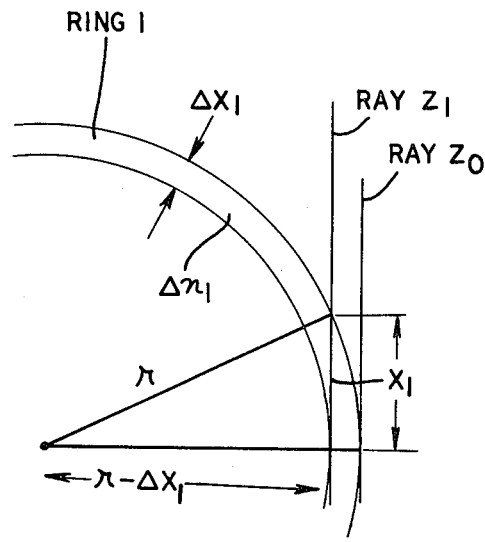
FIGS. 6 and 7 graphically illustrate the manner in which distances which light rays travel transversely through various cylindrical or ring-like portions of an optical fiber core may be calculated in accordance with the invention.

In FIG. 4 ray $Z_0$ is seen to pass tangentially to the core periphery and to be represented at point $z_o$ on the fringe line. Ray $Z_1$ is seen to pass through the outermost cylindrical ring 1 tangentially to the interface of abstract rings 1 and 2. In doing so the ray travels a distance of $2X_1$ towards the mirror and $2X_1$ away from it. The value for $X_1$ may be easily calculated by the application of the right triangle law as shown in FIG. 6. Since ring thickness $\Delta X_1$ is a selected value, and core radius r is known, $x_1 = \sqrt{r^2 - (r - \Delta x_1)^2}$.

Figure 7:
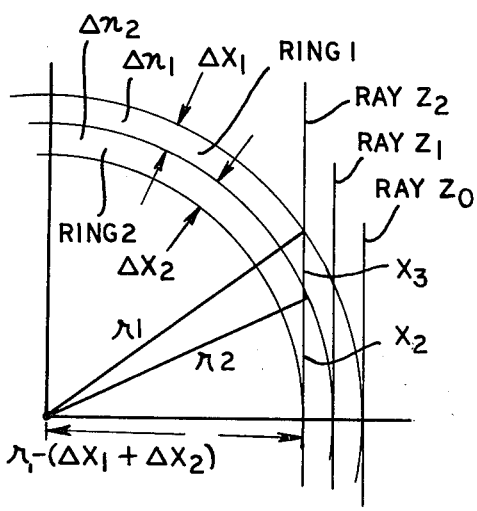

The just described procedure is next repeated for all of the other rings. Thus, as shown in FIG. 7, it is seen that ray $Z_2$ travels through ring 1 a distance of $4X_3$ and through ring 2 a distance of $4X_2$. Again, the values of both $X_3$ and $X_2$ may be calculated by the right triangle law. Thus, $X_2 = \sqrt{r_1^2 - [r_1 - (\Delta X_1 + \Delta X_2)]^2}$ while $X_3$ is derived from the equation $(X_2 + X_3)^2 + [r_1 - (\Delta X_1 + \Delta X_2)]^2 = r_1^2$. As the value of the index of refraction of the outermost ring 1 is determined prior to the determination of distance thus of travel time of ray $Z_2$, the only unknown in correlating the point $z_2$ on the fringe line with index of refraction of the core is the refractive index of ring 2.

The measurable fringe line shift is, of course, related to the time taken by light rays to traverse the various concentric rings of which the core is abstractly composed. The distance travelled in the outermost ring is related to the measured fringe shift and to the index of refraction of the outermost ring by the expression $4X_1 \Delta N_1 = (Q/L)\lambda$ where $\lambda$ is the light wavelength, Q is the fringe shift, L the fringe line spacing, $\Delta N_1$ is the index of the outer ring minus the cladding index, and $X_1$ is the distance designated in FIG. 4. Computation is thus followed for each successive layer or ring inwardly by application of this basic equation until the entire profile of the core is developed. In order to utilize the basic equation in calculating $\Delta N$ values throughout the core it is best expressed as a general equation as now described.

First, the equation for calculating the distance $X_{z,j}$ that any ray z travels in any ring J is expressed, with the dual pass method employed as $X_{z,j} = 4\{[r_{J-1}^2 - r_z^2]^{\frac{1}{2}} - [r_J^2 - r_z^2]^{\frac{1}{2}}\}$. For the case $X_{z,1}$ $r_o$ is the outer core radius. Where the single pass method is used the factor 4, of course, becomes 2. At a particular ray position z the fringe shift $Q_z$ is merely a summation of the effects of the ray passing through the various rings aligned therewith as illustrated in FIG. 4. This can therefore be expressed as $$Q_z = \frac{L}{\lambda}\left(\Delta n_z X_{z,z} + \sum_{j=1}^{j=Z-1} \Delta n X_{z,J}\right).$$

Where $\Delta N_z$ is the relative refractive index of a ring z in terms of the relative index values of all preceeding rings, $\Delta N_j$ is the difference between the refractive index value of a ring J and the cladding index, and $\lambda$ is the wavelength of the light employed. Here, the $\Delta N_z X_{z,z}$ factor represents the fringe shift caused by the z ray passing through the z ring while the factor $$\sum_{j=1}^{j=Z-1} \Delta n_J X_{z,J}$$

represents the shift caused by all of the preceeding outer rings. By rearranging the equation $\Delta N_z$ may be solved as $$\Delta n_z = \frac{1}{X_{z,z}}\left(\frac{\lambda Q_z}{L} - \sum_{J=1}^{j=Z-1} \Delta n_J \cdot X_{z,J}\right)$$

This general equation is then used to calculate $\Delta N_z$ for successive inner rings until the entire core is profiled.

Actual results produced by just described procedure on eight fiber samples using the single pass system and method are presented in Table I.

TABLE I

| FIBER SAMPLE | $\Delta n$ | CORE-RADIUS MICRONS | ALPHA | FIT ERROR % | FIT REGION MICRONS |
|---|---|---|---|---|---|
| SLAB #1 | .0202 | 22.29 | 2.23 | 1.5 | 5-20 |
| WHOLE #1 | .01903 | 21.39 | 2.36 | 2.3 | 5-20 |
| SLAB #2 | .0183 | 27.67 | 2.32 | 1.1 | 5-25 |
| WHOLE #2 | .0174 | 27.07 | 2.35 | 0.8 | 5-25 |
| SLAB #3 | .0227 | 27.89 | 1.49 | 1.0 | 5-25 |
| WHOLE #3 | .0220 | 26.69 | 1.57 | 1.0 | 5-25 |
| SLAB #4 | .0230 | 27.22 | 1.48 | 0.8 | 8-25 |
| WHOLE #4 | .0221 | 27.04 | 1.45 | 0.8 | 8-25 |
| SLAB #5 | .0207 | 22.94 | 2.17 | 0.9 | 4-21 |
| WHOLE #5 | .0194 | 22.31 | 2.39 | 1.9 | 4-21 |
| SLAB #6 | .0184 | 25.60 | 2.25 | 1.2 | 5-22 |
| WHOLE #6 | .0185 | 24.76 | 2.43 | 2.7 | 5-22 |
| SLAB #7 | .0212 | 26.74 | 1.70 | 0.6 | 12-25 |
| WHOLE #7 | .0228 | 26.94 | 1.75 | 0.6 | 12-25 |
| SLAB #8 | .0094 | 24.95 | 2.06 | 0.7 | 3-22 |
| WHOLE #8 | .0089 | 24.90 | 2.04 | 1.47 | 3-22 |

Figure 8:
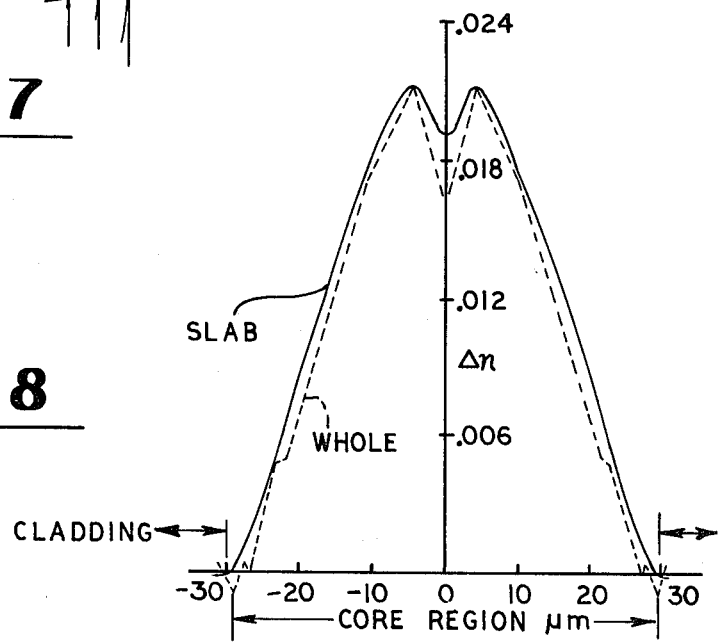
FIG. 8 is a graphic illustration of an index of refraction profile made in accordance with the invention and compared with that utilizing the prior art slab method.

In Table I $\Delta N$ indicates the amount that the refractive index at core the center exceeds the cladding index. The core-radius is from core center to periphery. The alpha ($\alpha$) values were derived from a curve fitting procedure which utilized about 40 values of $\Delta N$ at some 40 different points of fringe line shifts from core center to periphery within the fit bounds indicated. The fit regions indicate the core radial distance to which the curve fitting was applied. The fit error denotes deviation of the index profiles from the fitted curves for the present method on whole fibers and the prior art conventional slab method. FIG. 8 itself depicts the profile of sample No. 3 in Table I wherein the solid line follows slab measurements and the broken line that of the single pass method of this invention. Any lack of symmetry in FIG. 8 is due to the fact that slab data was obtained radially from opposed sides of core center while the whole sample method assumes circular symmetry. Since these profiles are not ideal alpha distributions, the value of alpha depends on the limits of the region over which the fit is made. The table shows the average difference of the maximum $\Delta N$ values and the $\alpha$ values as being about 4%.

In addition to the good agreement of the fitted data, the index profiles themselves are in excellent correspondence. The method tends to display more clearly the areas near the core center than has heretofore been achieved. This is due to the fact that all fluctuations are magnified and therefore so are systematic ones near the core center. The central index depression is also resolved to a greater degree since this region, with the prior art slab technique, possesses a large index gradient that cannot be resolved by the interference fringe passing through it. The depression depth displayed by the new method instead depends on the proximity of a vertical scanning line to the fiber axis which accounts for profile variations observed here.

We thus see that a new method is provided for determining an index of refraction profile of an optical fiber.

With this method the index profile may be determined in a manner non-destructive to the fiber itself with transverse illuminations forming an interferogram. The method is workable on both stepped and graded index cores and may even be employed in preforms. Of real significance is the fact that the profile is derived from an interferogram in a manner that does not require assumption of any particular functional shape of the index distribution, and thus with substantially improved accuracy.

It should be understood that the just described embodiments merely illustrate principles of the invention in preferred forms. Many modifications, deletions and additions may, of course, be made thereto without departure from the spirit and scope of the invention.

What is claimed is:

1. The method of determinig an index of refraction profile of the core of an optical fiber having a substantially cylindrical core encased within a surrounding cladding comprising the steps of:
   (a) forming an interferogram with a beam of radiant energy passing transversely through the optical fiber with the interferogram having a pattern of mutually spaced interference fringe lines shifted from a reference line distances determined by differences between indices of refraction radially through the fiber core and that of the fiber cladding;
   (b) measuring the interferogram fringe line shift at a plurality of points along a fringe line corresponding to a series of mutually parallel ray chord paths extending through the core at mutually diverse minimum radial distances from the core axis; and
   (c) sequentially calculating from core peripheral region inwardly towards the core center that portion of the measured fringe line shift attributable to discrete differences in indices of refraction of cylindrical core ring portions of thicknesses defined by successive minimum radial distances in the series of ray paths and that of the cladding.

2. The method of determining an optical fiber index of refraction profile in accordance with claim 1 wherein step (a) the beam of radiant energy is passed once transversely through the optical fiber.

3. The method of determining an optical fiber index of refraction profile in accordance with claim 1 wherein step (a) the beam of radiant energy is passed twice transversely through the optical fiber.

4. The method of determining an optical fiber index of refraction profile in accordance with claim 1 wherein the calculations of step (c) includes repeated application of the right triangle law to determine time to light ray travel in the cylindrical ring portions of the core.

5. The method of determining an optical fiber index of refraction profile in accordance with claim 1 wherein the calculations of step (c) for the index of refraction of any one cylindrical core ring portion includes the indices of refraction previously calculated for all cylindrical core ring portions about said one cylindrical core ring portion.

6. The method of determining an optical fiber index of refraction profile in accordance with claim 1, 2 or 3 wherein step (c) the discrete difference $\Delta N_z$ in the index of refraction of each core ring portion in terms of the index of refraction values of all outermore ring portions at any ring z, is determined by application of the general equation:

$$\Delta n_Z = \frac{1}{X_{Z,Z}} \left( \frac{\lambda Q_Z}{L} - \sum_{j=1}^{j=Z-1} \Delta n_j X_{Z,J} \right)$$

where $\Delta N_j$ is the difference between the refractive index value of a ring J and the cladding index, $\lambda$ is the wavelength of the radiant energy, $Q_z$ is the fringe shift at the position of a ray passing through ring z, l is the separation parallel fringe lines in the cladding, $X_{z,z}$ is the distance the ray travels in ring z and $X_{z,J}$ is the distance the ray travels in ring J.

7. The method of determining an optical index of refraction profile in accordance with claim 1 further comprising the step of (d) plotting the index of refraction profile correspondent with the sequence of calculations made in step (c).

* * * * *